US009301760B2

(12) United States Patent
Fox

(10) Patent No.: US 9,301,760 B2
(45) Date of Patent: Apr. 5, 2016

(54) DEVICES FOR SECURELY CLOSING TISSUE OPENINGS WITH MINIMIZED SCARRING

(71) Applicant: DermaClip US, LLC, Houston, TX (US)

(72) Inventor: Andrew D. Fox, Westborough, MA (US)

(73) Assignee: DermaClip US, LLC, Houston, TX (US)

( * ) Notice: Subject to any disclaimer, the term of this patent is extended or adjusted under 35 U.S.C. 154(b) by 230 days.

(21) Appl. No.: 14/068,763

(22) Filed: Oct. 31, 2013

(65) Prior Publication Data
US 2014/0058444 A1 Feb. 27, 2014

Related U.S. Application Data

(63) Continuation of application No. PCT/US2012/036265, filed on May 3, 2012.

(60) Provisional application No. 61/481,986, filed on May 3, 2011.

(51) Int. Cl.
*A61B 17/08* (2006.01)
(52) U.S. Cl.
CPC ............ *A61B 17/08* (2013.01); *A61B 2017/081* (2013.01); *A61B 2017/086* (2013.01)
(58) Field of Classification Search
CPC ................. A61B 17/08; A61B 17/085; A61B 2017/081; A61B 2017/088
USPC .................................. 606/215, 216, 217, 218
See application file for complete search history.

(56) References Cited

U.S. PATENT DOCUMENTS

| 345,541 A | 7/1886 | Reichardt |
| 363,538 A | 5/1887 | Penny |
| 1,774,489 A | 8/1930 | Sarason |
| 2,196,286 A | 4/1940 | Barsky |

(Continued)

FOREIGN PATENT DOCUMENTS

| CN | 1635852 | 7/2005 |
| CN | 101229071 | 7/2008 |

(Continued)

OTHER PUBLICATIONS

International Searching Authority, International Search Report—International Application No. PCT/2009/038188, dated Aug. 28, 2009, together with the Written Opinion of the International Searching Authority, 11 pages.

(Continued)

*Primary Examiner* — Tuan V Nguyen
(74) *Attorney, Agent, or Firm* — Remenick PLLC

(57) ABSTRACT

Devices, tools, systems, kits and methods for closing a tissue opening non-invasively are presented. The devices include a tissue closure device that reliably induces eversion of tissue edges that define a tissue opening. The devices may be used in combination with an applicator tool to provide easy and uniform apposition of the tissue closure devices across the tissue opening. Further embodiments provide for releasable locking of the tissue closure devices, allowing for drainage of wound edema and/or treatment of infection, without removal and reapplication of the devices. Still further embodiments allow for the passing of moisture or other substances that may collect under a tissue closure device.

12 Claims, 6 Drawing Sheets

(56) References Cited

U.S. PATENT DOCUMENTS

| | | | |
|---|---|---|---|
| 3,288,137 A | 11/1966 | Lund | |
| 3,487,836 A | 1/1970 | Niebel et al. | |
| 3,863,640 A | 2/1975 | Haverstock | 128/335 |
| 3,926,193 A | 12/1975 | Hasson | 128/335 |
| 3,971,384 A | 7/1976 | Hasson | 128/335 |
| 3,983,878 A | 10/1976 | Kawchitch | 128/335 |
| 4,114,624 A | 9/1978 | Haverstock | 128/335 |
| 4,141,363 A | 2/1979 | James et al. | 128/335 |
| 4,423,731 A | 1/1984 | Roomi | 128/335 |
| 4,467,805 A | 8/1984 | Fukuda | 128/334 |
| 4,526,173 A | 7/1985 | Sheehan | 128/335 |
| 4,535,772 A | 8/1985 | Sheehan | 128/337 |
| 4,539,990 A | 9/1985 | Stivala | 128/335 |
| 4,605,005 A | 8/1986 | Sheehan | 128/335 |
| 4,702,251 A | 10/1987 | Sheehan | 128/335 |
| 4,815,468 A | 3/1989 | Annand | 128/335 |
| 4,924,866 A | 5/1990 | Yoon | 128/335 |
| 4,973,466 A | 11/1990 | Reich | 424/426 |
| 5,176,703 A | 1/1993 | Peterson | 606/216 |
| 5,259,835 A | 11/1993 | Clark et al. | 602/48 |
| 5,263,973 A | 11/1993 | Cook | 606/216 |
| 5,486,196 A | 1/1996 | Hirshowitz et al. | 606/218 |
| 5,562,705 A | 10/1996 | Whiteford | 606/215 |
| 5,571,138 A | 11/1996 | Blomqvist et al. | 606/218 |
| 5,733,305 A | 3/1998 | Fleischmann | 606/213 |
| 5,843,123 A | 12/1998 | Brazeau | 606/213 |
| 6,010,524 A | 1/2000 | Fleischmann | 606/213 |
| 6,106,544 A | 8/2000 | Brazeau | 606/213 |
| 6,152,874 A * | 11/2000 | Looney | A61B 17/0206 600/214 |
| 6,176,868 B1 | 1/2001 | Detour | 606/215 |
| 6,329,564 B1 | 12/2001 | Lebner | 602/41 |
| 6,559,350 B1 | 5/2003 | Tetreault et al. | 602/42 |
| 6,596,917 B2 | 7/2003 | Oyaski | 602/43 |
| 7,361,185 B2 | 4/2008 | O'Malley et al. | 606/215 |
| 7,429,265 B2 | 9/2008 | O'Malley et al. | 606/215 |
| 8,157,839 B2 | 4/2012 | Riskin et al. | 606/216 |
| 2002/0019649 A1 | 2/2002 | Sikora et al. | 606/232 |
| 2005/0033215 A1 | 2/2005 | Lebner | 602/54 |
| 2008/0027484 A1 | 1/2008 | Lee et al. | 606/215 |
| 2009/0036922 A1 | 2/2009 | Riskin et al. | |
| 2009/0177227 A1 * | 7/2009 | Warren | A61B 17/085 606/217 |
| 2011/0022082 A1 | 1/2011 | Burke et al. | 606/214 |

FOREIGN PATENT DOCUMENTS

| | | | |
|---|---|---|---|
| DE | 2447681 | 4/1976 | A61F 13/00 |
| EP | 0957774 | 6/2002 | A61B 17/03 |
| GB | 1401877 | 8/1975 | A61B 17/08 |
| WO | WO 96/10954 | 4/1996 | A61B 17/08 |
| WO | WO 96/29013 | 9/1996 | A61B 17/03 |
| WO | WO 99/42146 | 8/1999 | A61L 25/00 |
| WO | WO 01/40348 | 6/2001 | C08G 63/00 |
| WO | WO 2004/006782 | 1/2004 | |
| WO | WO 2006/026634 | 3/2006 | A61B 17/08 |
| WO | WO 2012/151366 | 11/2012 | A61B 17/03 |

OTHER PUBLICATIONS

International Searching Authority, International Search Report—International Application No. PCT/US2012/036265, dated Nov. 20, 2012, together with the Written Opinion of the International Searching Authority, 12 pages.
Chinese Office Action for Application No. 201280001681.2, dated Apr. 9, 2015.
Chinese Office Action for Application No. 201280001681.2, dated Aug. 1, 2014.
EP Search Report for PCT/US2012/036265, dated Jun. 8, 2015.
Australian Office Action for Application No. 2012250699, dated Nov. 12, 2015.

* cited by examiner

DEVICES FOR SECURELY CLOSING TISSUE OPENINGS WITH MINIMIZED SCARRING

CROSS-REFERENCE TO RELATED APPLICATIONS

The present application is a continuation of Patent Cooperation Treaty Application PCT/US2012/036265, filed May 3, 2012, which in turn claims the benefit of U.S. Provisional Patent Application Ser. No. 61/481,986, entitled "Devices for Securely Closing Tissue Openings with No Scarring," filed May 3, 2011, each of which are hereby incorporated herein by reference in its entirety.

TECHNICAL FIELD

This invention is directed to tissue closure devices, tools, systems, kits, and methods for tissue repair and closure. In particular, the invention is directed to devices and methods that safely and securely close wounded tissue openings and permit and encourage healing to occur.

BACKGROUND ART

Closure of tissue openings, such as, for example, for surgical incisions and accidental lacerations or wounds, is critical both to minimize the risk of infection and to promote optimal healing of the wound or incision. Both of these outcomes require rapid wound closure and careful skin edge approximation. Closing a tissue opening or wound requires a mechanism for drawing both sides of a tissue opening together to promote healing and to reduce the formation of scar tissue.

Previous wound closure systems included various categories of materials passed through the skin, such as staples and sutures, substances that cover skin edges and hold them adjacent, such as glues, and adherent structures, such as strips. Common methods for closing tissue openings caused by lacerations or surgical incisions are suturing and stapling. Both of these procedures are invasive, which can traumatize and compromise the integrity of the tissue opening and the nutrient blood supply to the healing tissue edges. They cause pain, increase the possibility of infection, expose the surgeon, as well as the patient, to blood-borne disease, leave behind scars, and require a follow-up visit for suture or staple removal. Surgical glue is also used, but has only been proven adequate for small wounds where skin edges are not widely separated or under tension during closure.

Typical techniques of suturing to minimize the resulting blemish that occurs during the healing process require a threshold of dexterity that many care providers do not possess. This is particularly true in emergency situations, which often require immediate treatment to secure the tissue opening to allow for transport or until such time as proper surgery is possible. Suturing even by a skilled surgeon punctures and stresses tissue causing scarring. An easy to use, suture-less tissue opening closure system would be a great benefit in many situations.

Scientific principles show that cosmetic outcome in wound healing is largely determined by apposition and eversion created during wound closure. Eversion is critically important as expected scar formation includes myofibril contraction, which ultimately draws the scar slightly below the surrounding skin level. This is often seen in surgical scars, which have divets or slight depressions in the center. Eversion prevents or at least minimizes this phenomenon by starting with slightly raised skin which lays flat after the universal process of contraction, which occurs at about 2-3 weeks after injury. The medical community generally recommends skin edge eversion to promote the least noticeable scar. Unfortunately, skin edge eversion and apposition is difficult to achieve with simple stitches or glues. More complex stitches and devices that promote adequate eversion and apposition are time consuming to place and are used in less than one case in one hundred. Additionally, conventional tissue closure devices for tissue do not allow for the breathing and the egress of tissue fluids. Often, the durability of the applied tissue device is compromised by the impervious barrier to moisture and other substances beneath polymer components. This may lead to dislodgement of the tissue device.

SUMMARY OF THE EMBODIMENTS

The invention is directed to devices, systems and methods for closing surgical incisions and non-surgical wounds that provide for improved wound care. In accordance with an embodiment of the invention, a tissue closure device for non-invasively closing a tissue opening includes an assembled pair of substantially identical closure components. Each component includes a tissue attachment base with an attachment mechanism on a first side thereof to affix the attachment base to the skin. A standoff assembly is mounted on a second side of the attachment base of each component. A toothed pull-tab, having first and second ends, is coupled to the attachment base of each component through the standoff assembly and defines a longitudinal axis. The standoff assembly has a forward face, to which the first end of the pull-tab is affixed, and an opposed rearward face, the forward face including a sloped portion that is sloped rearward as it approaches the attachment base. Each component further includes a female connective element, mounted on the second side of the attachment base, and which is built into the standoff assembly, that receives and engages the pull-tab from the other component and into which the pull-tab from the other component has been placed. Each pull-tab has a length sufficient to reach and be received by the female connective element of the other closure component. The second end of the pull-tab protrudes from the female connective element and defines an opening configured so as to releasably receive one of a corresponding pair of arms of an applicator tool, such that the device can be loaded onto the applicator tool in a position that straddles the arms of the applicator tool. When the loaded assembled pair is affixed to the skin with each of the attachment bases disposed on an opposite side of the tissue opening, the applicator tool can be manipulated to adjust the spacing between the arms and causes the second ends of the pull-tabs to be pulled away from each other. This brings the sloped portions of the forward faces of the components into substantial contact with one another at a location of contact, causing each standoff assembly to pivot about the location of contact, inducing eversion of tissue edges that defined the opening.

In accordance with another embodiment of the invention, a system for non-invasively closing a tissue opening includes a plurality of the tissue closure devices described in the above embodiment, and further includes an applicator tool for applying the tissue closure devices to a tissue opening. The applicator tool includes an operator end configured to be grasped by a user. A pair of arms are mounted to the operator end through a linkage assembly. The linkage assembly is configured to adjust spacing between the arms while maintaining the arms in parallel alignment. Manipulation of the linkage assembly effected at the operator end adjusts the spacing between the pair of arms. The arms and the linkage assembly are dimensioned and configured to receive corresponding second ends of pull-tabs of the closure devices. More particularly, as described in the above embodiment, the second ends of the closure devices include and define an opening configured so as to releasably receive one of a corresponding pair of arms of the applicator tool such that the devices can be loaded onto the applicator tool in a position that straddles the arms of the applicator tool. The applicator tool moves between a first position in which the closure devices can be loaded onto the arms of the applicator, and a second position in which the pull-tabs on one side have been pulled away from those on the other side, after the closure devices have been loaded onto the arms of the applicator, and have been placed on the tissue opening, and the operator chooses to effectuate tissue closure.

In accordance with another embodiment of the invention, an applicator tool for applying a plurality of tissue closure devices to a tissue opening is provided. The applicator tool includes an operator end configured to be grasped by a user. A pair of arms are mounted to the operator end through a linkage assembly and are configured to adjust spacing between the arms while maintaining the arms in parallel alignment. Manipulation of the linkage assembly effected at the operator end adjusts the spacing between the pair of arms. The arms and the linkage assembly are dimensioned and configured to receive corresponding second ends of pull-tabs of each of the a plurality of closure devices. The applicator tool moves between a first position in which the closure devices can be loaded on the arms of the tool and a second position in which the pull-tabs on one side can be pulled away from those on the other side, after the closure devices have been loaded onto the arms of the applicator, and have been placed on the tissue opening, and the operator chooses to effectuate tissue closure.

In accordance with further embodiments of the invention, a female connective element of a tissue closure device may have a releasable tab-locking mechanism configured to releasably lock the pull-tab in position. The releasable tab locking mechanism may include a releasable finger having a tip that engages against such pull-tab. The finger may have an unreleased position wherein the tip engages against such pull-tab and a released position wherein the pull-tab can be freely moved, the finger being biased in the unreleased position. In various embodiments, a ratchet/piston locking mechanism may be provided that allows for precise closure and locking of the paired components. By depressing the piston, the locking mechanism is securely unlatched. The releasable tab-locking mechanism may be manipulated by hand, or may require a tool, for example, tweezers or a needle. More particularly, in various embodiments, the tab-locking mechanism may include a hollow recess. A tool, for example a needle, can be used to unlock the locking mechanism, for example by engaging the end of the needle into the hollow recess of the locking mechanism, applying force to the locking mechanism through the tool, and with that force unlocking the locking mechanism. The releasable tab-locking mechanism allows for drainage of wound edema and/or the treatment of infection, without removal and reapplication of the device. Such a feature can also be helpful when a wound needs to be temporarily left open to facilitate healing.

In accordance with further embodiments of the invention, the attachment base of a tissue closure device may be porous to allow for tissue breathing and the egress of tissue fluids. In various embodiments, the tissue closure device may have predefined holes placed on the attachment base that is seated on the tissue opening. Human tissues, unlike many other mammalian species, respire, produce oils and moisture. These physiologic processes result in premature dislodgement and migration of the device and thereby render the device ineffective. This is overcome by placement of a critical mass of openings to allow for evaporation and drainage of said fluids and gasses without effecting adhesive performance.

In accordance with further embodiments of the invention, the tissue closure device may be made of a biodegradable polymer. The attachment mechanism may include at least one of a hook and an adhesive. A strip of a plurality of tissue closure devices may be provided, wherein the tissue closure devices are held in spaced relationship to one another along at least one strip. For example, the tissue closure devices may be held in a parallel spaced relationship to one another along at least one strip.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Definitions

As used in this description and the accompanying claims, the following terms shall have the meanings indicated, unless the context otherwise requires:

A "tissue opening" refers to any surgical incision, accidental laceration or other form of injury. A tissue opening may be a wound in the skin, or to a tissue within a living or dead body, such as an organ. The tissue opening may be associated with any animal, including human and non-human animals. In some embodiments, the tissue opening may be associated with a mammal or a non-human mammal. A tissue opening may be of any shape or size.

"Apposition" refers to the proper alignment of skin edges to prevent gaps or mismatch.

"Eversion" is the raising of skin edges during the healing process.

In illustrative embodiments of the invention, devices, tools, systems, kits and methods for closing a tissue opening non-invasively are presented. The devices include a tissue closure device that reliably induces eversion of tissue edges that define a tissue opening. The devices may be used in combination with an applicator tool to provide easy and uniform apposition of the tissue closure devices across the tissue opening. Further embodiments provide for releasable locking of the tissue closure devices, allowing for drainage of wound edema and/or treatment of infection, without removal and reapplication of the devices. Still further embodiments allow for the passing of moisture or other substances that may collect under a tissue closure device. Details are discussed below.

Figure 1A:
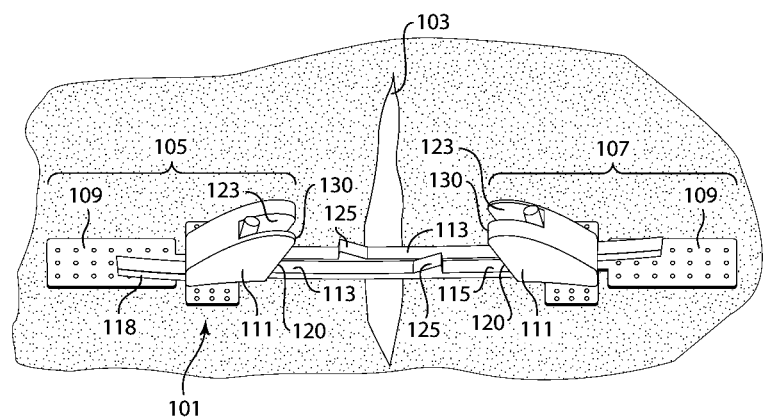
FIG. 1(a) shows an oblique view of a tissue closure device applied to a tissue opening prior to an operator effectuating tissue closure, in accordance with an embodiment of the invention.
Figure 1B:
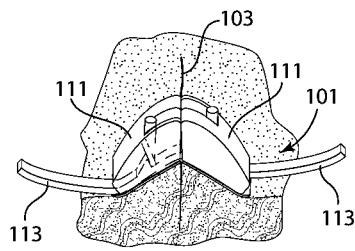
FIG. 1(b) shows an oblique view of the tissue closure device of FIG. 1(a) after the operator effectuates tissue closure.

FIG. 1(a) shows an oblique view of a tissue closure device 101 applied to a tissue opening 103 prior to an operator effectuating tissue closure, while FIG. 1(b) shows an oblique view of the tissue closure device of FIG. 1(a) after the operator effectuates tissue closure, in accordance with various embodiments of the invention. The tissue closing device 101 may be made of various materials, including, without limitation, plastic, metal, polypropelene, high-density polypropelene, and other polymers or thermoplastic materials, or combinations thereof. In various embodiments, the materials used for the tissue closure device 101 will be light, strong, and/or waterproof. It is possible that with some materials, the tissue closure device 101 may be cleaned and sterilized for reuse. The tissue closure device 101 may be applied under sterile or medically clean conditions depending on the type of wound and according to the best judgment of the healthcare provider. In some embodiments, the tissue closure device 101 (or one or more members thereof) includes an agent, such as for example a chemical, to detect and signal impending infection. Alternatively, in some embodiments, such an agent may be added to or above the closure during or after the procedure. In some embodiments the wound closure components may be made of bioabsorbable materials, such as a polysaccharide material. Bioabsorbable materials may advantageously be used to close a tissue opening within a living body, whereupon extra surgery is not needed for removal of the tissue closure device 101.

The tissue closure device 101 includes an assembled pair of substantially identical closure components 105 and 107. Each of the closure components 105 and 107 includes a tissue attachment base 109 with an attachment mechanism on a first side (e.g., the underside of the tissue attachment base 109). The attachment mechanism is used to affix the attachment base 109 to, without limitation, the skin or other tissue. The attachment mechanism may be an adhesive. The adhesive may be designed such that the user has some time to make minor placement adjustments before the adhesive adheres to the skin surface. This time can range from approximately ten seconds to approximately three minutes, and in a preferred embodiment is approximately one minute. The adhesive may be, without limitation, a pressure sensitive adhesive. In various embodiments, the attachment mechanism may include one or more hooks to affix the attachment base to the skin or other tissue.

A standoff assembly 111 is mounted on a second side of the attachment base 109 of each closure component 105 and 107. A pull-tab 113, having first and second ends 115 and 118, respectively, is coupled to the attachment base 109 through the standoff assembly 111 and defines a longitudinal axis. The standoff assembly 111 has a forward face 120, to which the first end 115 of the pull-tab 113 is affixed, and an opposed rearward face. The forward face 120 includes a sloped portion that is sloped rearward as it approaches the attachment base 109.

Each of the closure components 105 and 107 also include a female connective element 123 mounted on the second side of the attachment base 109 and built into the standoff assembly 111. The female connective element 123 receives and engages the pull-tab 113 from the other component. When the closure components 105 and 107 are engaged, the pull-tab 113 of each closure component 105 and 107 member passes through the female connective element 123 of the other member. The pull-tab 113 has teeth 125 rising from its upper surface. Upon entry of a pull-tab 113 into its associated female connective element 123, the female connective element 123 prevents teeth 125 passing through the female connective unit 123 from backing out. As described in further detail below, the female connective element 123 may include a releasable tab-locking mechanism.

As the pull-tabs 113 are pulled through female connective element 123 of the other closure component 105 and 107, the closure components 105 and 107 and hence the edges of the tissue opening to which the attachment base 109 is adhered to, move closer to each other. Further pulling brings the sloped portions of the forward faces 120 of the closure component components 106 and 107 into substantial contact with one another at a location of contact 130, whereupon each standoff assembly 111 pivots about the location of contact 130, as shown in FIG. 1(b). When this occurs, respective portions of the undersurfaces of each tissue attachment base 109, which have adhesive covering and which are adhered to the skin or other tissue during use, are lifted, inducing eversion of the tissue edges that define the tissue opening. To facilitate wound edge eversion, the tissue closure device preferably has pull-tabs 113 in the lower one third of the height of each standoff assembly 111, and preferably has locations of contact 125 in the top one third of the height of each standoff assembly 111.

It is preferred that the tissue opening to be treated is smaller than the length of the pull-tabs. However, even for a tissue opening larger than the length of the pull-tabs, the members can be applied to both sides of the opening and manually brought together to allow the pull-tabs to engage with the respective openings on paired members. A further benefit of certain embodiments of the invention is that wounds can be closed over the course of multiple application steps. The person applying the tissue closure devices can choose to engage the members and close the tissue opening either partially or fully.

Figure 2:
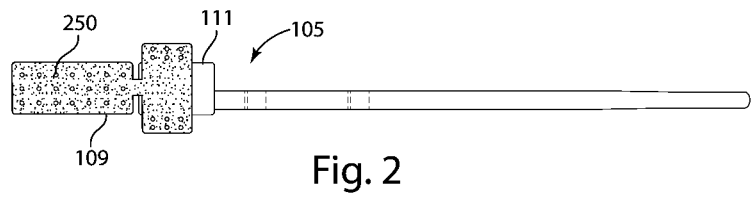
FIG. 2 shows a bottom view of a closure component, in accordance with an embodiment of the invention.
Figure 3:
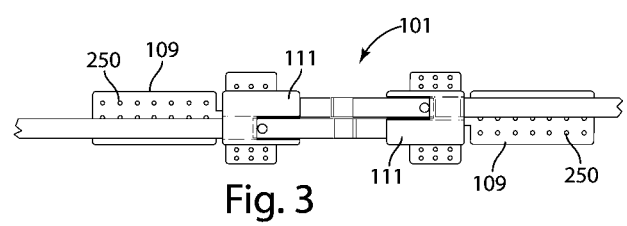
FIG. 3 shows a top view of an engaged tissue device, in accordance with an embodiment of the invention.

FIG. 2 shows a bottom view of closure component 105, while FIG. 3 shows a top view of the engaged tissue closure device 101, in accordance with various embodiments of the invention. The attachment base 109 of the closure devices 105 and 107 may be porous to allow for tissue breathing and the egress of tissue fluids. Human tissues, unlike many other mammalian species, respire, produce oils and moisture. These physiologic processes may result in premature dislodgement and migration of the device 101 and thereby render the device 101 ineffective. This may be overcome by making the attachment base 109 porous. For example, the attachment base 109 may include porous material, and/or a critical mass of one or more predefined holes 250, that allow for tissue breathing and the egress of tissue fluids and/or gasses without effecting the adhesive performance of the device 101.

The female connective element 123 of each closure device 105 and 107 may have a releasable tab-locking mechanism configured to releasably lock the pull-tab 113 in position. Such a locking mechanism may be unlocked by a tool, for example, tweezers or a needle, or in some embodiments a human finger, and the lock can subsequently be reengaged on the pull-tab to relock the pull-tab. The releasable tab-locking mechanism advantageously allows for drainage of wound edema and/or the treatment of infection, without removal and reapplication of the device. Such a feature can also be helpful when a tissue opening needs to be temporarily left open to facilitate healing.

Figure 4A:
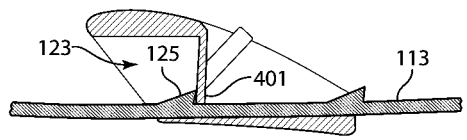
FIG. 4(a) shows a cross-section of a female connective element in an unreleased position, in accordance with an embodiment of the invention.
Figure 4B:
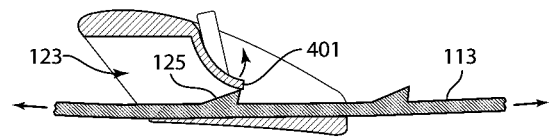
FIGS. 4(b) and 4(c) show cross-sections of the female connective element of FIG. 4(a) in released positions, wherein the pull-tab can be freely moved.
Figure 4C:
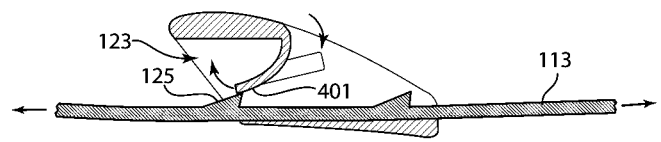

FIG. 4(*a*) shows a cross-section of a female connective element 123 in an unreleased position, in accordance with an embodiment of the invention. Illustratively, the releasable tab locking mechanism may include a releasable finger 401. The releasable finger 401 may be, for example, positioned in a recess, such that a tool is required to manipulate the finger 401. In other embodiments the finger 401 may protrude from the recess such that it can be manipulated without a special tool. The releasable finger 401 may have a tip that can engage against the teeth 125 the pull-tab 113. For example, in the unreleased position, the tip of the finger 401 may engage against a tooth 125 on the pull-tab, the finger 401 being biased in the unreleased position. By rotating the finger forward or backward, as shown in FIGS. 4(*b*) and 4(*c*) respectively, a released position is obtained wherein the pull-tab can be freely moved.

Figure 5:
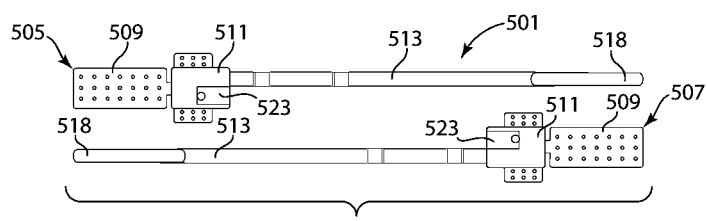
FIG. 5 shows a top view of a pair of closure devices of a tissue closure device in an unengaged position, in accordance with an embodiment of the invention.
Figure 6:
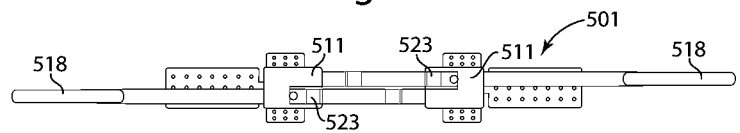
FIG. 6 shows a top view of the tissue closure device of FIG. 5 in an engaged position.
Figure 7:
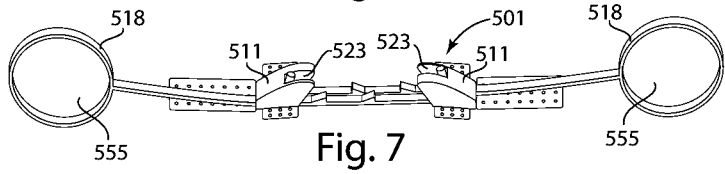
FIG. 7 shows an oblique view of the tissue closure of FIG. 5 in an engaged position.

In illustrative embodiments of the invention, FIG. 5 shows a top view of a pair of closure devices 505 and 507 of a tissue closure device 501 in an unengaged position. FIG. 6 shows a top view of the tissue closure device 501 of FIG. 5 in an engaged position, and FIG. 7 shows an oblique view of the tissue closure device 501 of FIG. 5 in an engaged position. As shown in FIGS. 5-7, the second end 518 of each pull-tab 513 defines an opening 555. When the tissue closure device 501 is engaged, the second end 518 of each pull-tab 513 protrudes from the female connective element 523 of the other closure component. The opening 555 defined by the second end 518 is configured so as to releasably receive one of a corresponding pair of arms of an applicator tool. The tissue closure device 501 can thus be loaded onto the applicator tool in a position that straddles the arms of the applicator tool, so that, when the loaded assembled pair of closure devices 505 and 507 is affixed to the skin or other tissue, with each of the attachment bases 509 disposed on an opposite side of the tissue opening, manipulation of the applicator tool adjusts the spacing between the arms and causes the second ends 518 of the pull-tabs 513 to be pulled away from each other. This in turn, brings the sloped portions of the forward faces of the components into substantial contact with one another at a location of contact, with each standoff assembly 511 pivoting about the location of contact, so as to induce eversion of tissue edges that defined the opening.

As used in this description and the accompanying claims, the opening 555 defined by the second ends 518 of each pull-tab 513 may include any type of opening capable of receiving an arm of the applicator tool, such that application tool is capable of pulling the second ends 518 of corresponding pull-tabs 513 away from each other. For example, and without limitation, the opening 555 defined by the second ends 518 of each pull tab 513 may be of any shape, and may or may not be fully enclosed by the second end 518 of the pull-tab 513. Examples of an opening that is not fully enclosed include, without limitation, a hooked J or C shaped opening.

The tissue closure device may be manufactured and provided to an operator in the engaged position, such that the second end already protrudes from the female connective element of the other closure component. Alternatively, the tissue closure device may be provided to an operator in the unengaged position, with the second end of each pull tab being dimensioned and/or having enough flexibility so as be capable of being passed through the female connective element of the other closure component.

Figure 8:
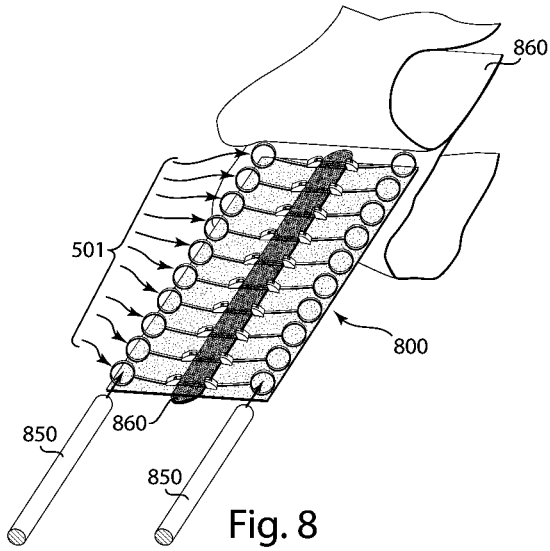
FIG. 8 shows an oblique view of a strip of a plurality of tissue closure devices of FIGS. 5-7, that are about to receive arms of an applicator tool, in accordance with an embodiment of the invention.

FIG. 8 shows an oblique view of a strip 800 of a plurality of tissue closure devices 501 of FIGS. 5-7, that are about to receive arms 850 of an applicator tool, in accordance with an embodiment of the invention. The tissue closure devices 501 may be held in spaced relationship to one another along at least one strip 860. For example, the tissue closure devices 501 may be held in a spaced parallel relationship, such that the second ends of each tab align with one of the arms 850 of the applicator tool. In some embodiments opposing closure components may be placed at set intervals along the longitudinal axis of the tissue opening. In additional embodiments, the intervals can be wide with large gaps to allow wound drainage or can be narrow with small gaps to improve skin edge apposition.

As shown in FIG. 8, the strip 800 of tissue closure devices 501 may come pre-assembled in a package 860. Furthermore, the tissue closure devices 501 may be packaged with the applicator tool, and, without limitation, the tissue closure devices 501 already loaded onto the arms 850 of the applicator tool.

Figure 9:
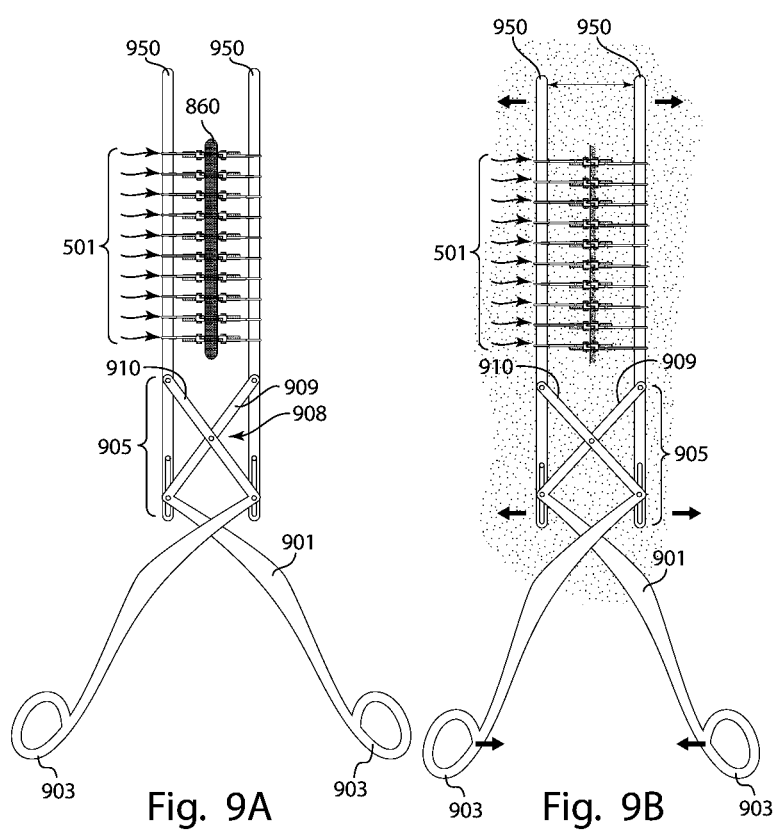
FIG. 9A shows an applicator tool, in a first position, loaded with tissue closure devices, in accordance with an embodiment of the invention.
FIG. 9B shows the applicator tool of FIG. 9A, in a second position, in accordance with an embodiment of the invention.

FIG. 9 shows an applicator tool 900, in a first position, loaded with tissue closure devices 501 for applying to a tissue opening, in accordance with an embodiment of the invention. The applicator tool 901 includes an operator end 903 configured to be grasped by a user. A pair of arms 950 is mounted to the operator end 903 through a linkage assembly 905. The linkage assembly 905 is configured to adjust spacing between the arms 950 while maintaining the arms 950 in parallel alignment. Manipulation of the linkage assembly 905 effected at the operator end 903 adjusts the spacing between the pair of arms 950. The arms 950 and the linkage assembly 905 are dimensioned and configured to receive corresponding second ends of pull-tabs a plurality of closure devices 501.

Illustratively, the linkage assembly 905 of the applicator tool 901 may include a scissor mechanism 908 that includes two pivoting scissor arms 909 and 910. Each of the scissor arms 909 and 910 is, at a first end that is distal the operator end 903, pivotally attached to a different arm 950 of the applicator tool. Additionally, each of the scissor arms 909 and 910 is, at a second end proximate the operator end, pivotally and slidably attached to a different arm 950 of the applicator tool, and furthermore, pivotally attached to different handles at the operator end 903.

By operator manipulation at the operator end 903, the applicator tool 901 can move between a first position (shown in FIG. 9A) in which the closure devices 501 can be/are loaded on the arms 950 of the tool 901, and a second position (shown in FIG. 9B) in which the pull-tabs on one side are pulled away from those on the other side, typically occurring after the closure devices 501 have been loaded onto the arms 950 of the applicator tool 901, and have been placed on the tissue opening.

Figure 10:
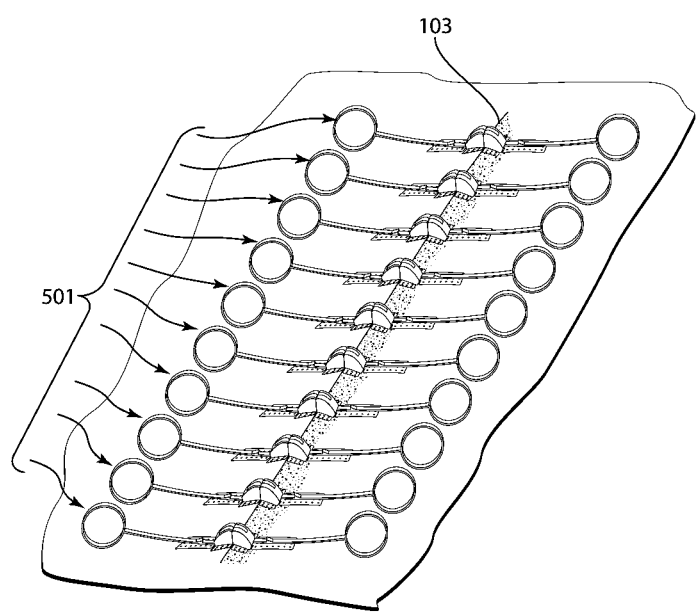
FIG. 10 is an oblique view of the closure devices after having been placed on the tissue opening, with the operator having furthermore effectuated tissue closure, in accordance with an embodiment of the invention.

FIG. 10 is an oblique view of the closure devices 501 after having been placed on the tissue opening, with the operator having furthermore effectuated tissue closure, in accordance with an embodiment of the invention. The applicator tool 901 pulling each end of pull-tabs 113 in parallel, at substantially the same time and with substantially the same force, throughout the application of the closure devices 501 to the tissue opening, provides quality apposition.

In various embodiments of the invention, the arms of the applicator tool may be physically attached to the closure devices, instead of being releasably received by openings defined at the second ends of the pull-tabs of each of the closure devices. For example, the closure devices and the arms of the applicator tool may be integrally formed or welded together. After having effectuated tissue closure, the user may cut, or otherwise remove the arms of the applicator tool from the closure devices.

Figure 11:
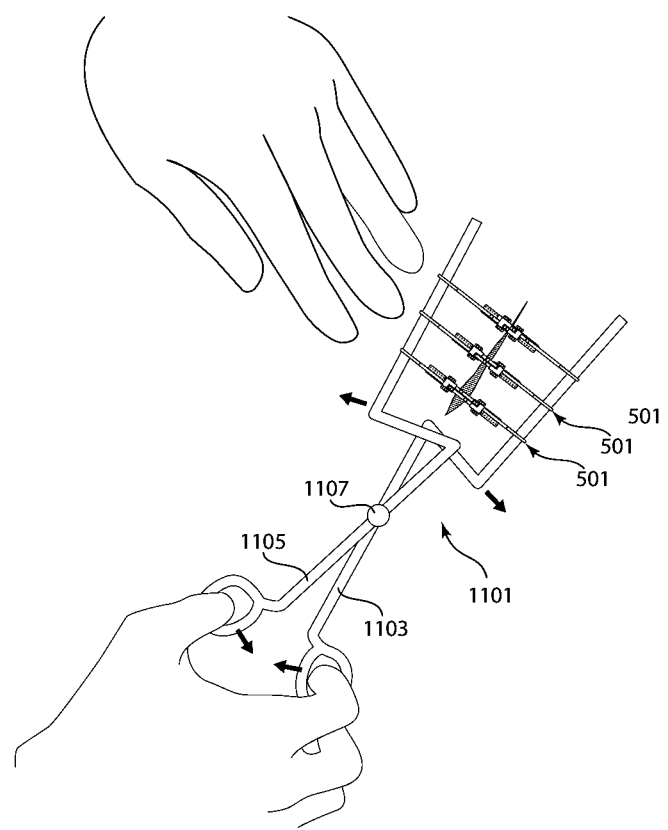
FIG. 11 shows an applicator tool, in accordance with an embodiment of the invention.

FIG. 11 shows a further embodiment of an applicator tool 1101. The arms 1103 and 1105 of the applicator tool 1101 rotate about a single pivot 1107, and thus the tool 1101 may be produced relatively cheaply. However, manipulation of the applicator tool 1101 causes the closure devices 501 to close in a non-parallel and uneven manner, and may lead to poor apposition.

Embodiments of the invention may be applied as follows. Assembly of the pairs of closure components that make up the closure device may be done prior to packaging and before the user receives the devices. Assembly may be done by pushing the pull-tabs of each closure component through the female connective element of its corresponding closure component, to initiate alignment and engage the paired closure devices. Adhesive backing may be applied to the tissue attachment base of each closure device, and an adhesive strip may be applied across the paired closure device to maintain proper alignment. The closure device may be loaded onto the applicator tool. Alternatively, the user may engage the pair(s) of closure components and/or load the closure device onto the applicator tool.

To apply the assembled closure devices to the tissue opening, the user may remove the adhesive backing from one closure component of the tissue closing device, or, in the case of multiple sets of paired closure components, from all closure components on one side of the engaged sets. The user may then place the closure component(s) with the adhesive backing removed on cleansed and dry skin so that their forward face(s) are abutting one edge of the tissue opening. The user then slowly brings the paired closure components together (e.g., by using the applicator tool), one closure component of each pair attached to the skin on one side of the wound and the other closure component each pair not yet attached to the skin. The user continues to bring the paired connections together until the second component of each paired component is placed abutting an opposite skin edge. The user then removes the adhesive backing from the second component(s) and places the second component(s) near the wound edge. The adhesive may be selected such that the user has some time to make minor placement adjustments before the adhesive adheres to the skin surface. This time can range from approximately ten seconds to approximately three minutes, and in a preferred embodiment is approximately one minute. After this time elapses, the user gently brings the edges of the tissue opening wound edges toward each other (e.g., by manipulating the applicator tool). The user can, if desired, unlock the closure component(s) by manipulating the tab-locking mechanism.

Depending on the type of adhesive used, the closure device will naturally exfoliate within approximately seven to ten days. Alternatively, a user can apply a solvent to the adhesive for more immediate removal. If desired, the paired closure components can be loosened a variable distance, for example from approximately 1 mm to approximately 10 mm to allow for drainage of fluids. The paired closure components can later tightened to re-close the tissue opening.

Other embodiments and uses of the invention will be apparent to those skilled in the art from consideration of the specification and practice of the invention disclosed herein. All references cited herein, including all publications, U.S. and foreign patents and patent applications, including U.S. application Ser. No. 11/217,127 and International Application No. PCT/US05/30890, both filed Aug. 31, 2005 and U.S. application Ser. No. 12/059,485 and International Application No. PCT/US09/38188, both filed Mar. 31, 2008, are specifically and entirely incorporated herein by reference in their entirety.

Although various exemplary embodiments of the invention have been disclosed, it should be apparent to those skilled in the art that various changes and modifications can be made that will achieve some of the advantages of the invention without departing from the true scope of the invention. These and other obvious modifications are intended to be covered by the appended claims.

What is claimed is:

1. A system for non-invasively closing a tissue opening, the system comprising:
 a plurality of tissue closure devices, each tissue closure device including:
  an assembled pair of substantially identical closure components, each component having:
  a tissue attachment base with an attachment mechanism on a first side thereof for affixing the attachment base to a patient's skin;
  a standoff assembly mounted on a second side of the attachment base;
  a toothed pull-tab, having first and second ends, coupled to the attachment base through the standoff assembly and defining a longitudinal axis, the standoff assembly having a forward face, to which the first end of the pull-tab is affixed, and an opposed rearward face, the forward face including a sloped portion that is sloped rearward as it approaches the attachment base;
  a female connective element, mounted on the second side of the attachment base and built into the standoff assembly, that receives and engages the pull-tab from the other component and into which the pull-tab from the other component has been placed,
  wherein each pull-tab has a length sufficient to reach and be received by the female connective element of the other closure component, the second end of the pull-tab protruding from the female connective element;
  wherein, when the assembled pair is affixed to the patient's skin with each of the attachment bases disposed on an opposite side of the tissue opening, the second ends of the pull-tabs can be pulled away from each other, to bring the sloped portions of the forward faces of the components into substantial contact with one another at a location of contact and to cause each standoff assembly to pivot about the location of contact, so as to induce eversion of tissue edges that defined the opening; and
 an applicator tool for applying the tissue closure devices to the tissue opening, the tool comprising:
  an operator end configured to be grasped by a user;
  a pair of arms, mounted to the operator end through a linkage assembly configured to adjust spacing between the arms while maintaining the arms in parallel alignment, and wherein manipulation of the linkage assembly effected at the operator end adjusts the spacing between the pair of arms;

wherein the arms and the linkage assembly are dimensioned and configured to receive corresponding second ends of pull-tabs of the closure devices, each of the second ends of the closure devices including and defining an opening configured so as to releasably receive one of a corresponding pair of arms of the applicator tool such that the devices can be loaded onto the applicator tool in a position that straddles the arms of the applicator tool, and wherein the applicator tool moves between a first position in which the closure devices can be loaded onto the arms of the applicator, and a second position in which the pull-tabs on one side have been pulled away from those on the other side, after the closure devices have been loaded onto the arms of the applicator, and have been placed on the tissue opening, and the operator chooses to effectuate tissue closure.

2. The system according to claim 1, including an array of the closure devices coupled to one another in a spaced apart parallel relationship, wherein the arms are configured to receive corresponding second ends of the pull-tabs of each device.

3. The system according to claim 1, wherein each pull-tab defines an opening proximate the second end, the opening configured such that one of the arms of the applicator tool can be inserted through the opening so as to releasably attach the applicator tool to the tissue closure device.

4. The system according to claim 1, wherein the female connective element includes a locking mechanism configured to lock the pull-tab in position.

5. The system according to claim 1, wherein the attachment base including a plurality of holes to allow for tissue breathing and the egress of tissue fluids.

6. The system according to claim 1, wherein the device is made of a biodegradable polymer.

7. The system according to claim 1, wherein the attachment mechanism includes at least one of a hook and an adhesive.

8. A method of closing a tissue opening of a patient using the system of claim 1, the method comprising;
affixing the assembled pair of each device such that each of their attachment bases is disposed on an opposite side of the tissue opening;
loading the openings of the second ends of the closure device onto corresponding arms of the applicator tool, the applicator tool in a first position;
moving the applicator tool between the first and a second position in which the second end of the pull-tabs on one side have been pulled away from those on the other side.

9. The method of claim 8, further comprising removing the application tool from the closure devices.

10. A system for non-invasively closing a tissue opening, the system comprising:
a plurality of tissue closure devices, each tissue closure device including:
an assembled pair of substantially identical closure components, each component having:
a tissue attachment base with an attachment mechanism on a first side thereof for affixing the attachment base to a patient's skin;
a standoff assembly mounted on a second side of the attachment base;
a toothed pull-tab, having first and second ends, coupled to the attachment base through the standoff assembly and defining a longitudinal axis, the standoff assembly having a forward face, to which the first end of the pull-tab is affixed, and an opposed rearward face, the forward face including a sloped portion that is sloped rearward as it approaches the attachment base;
a female connective element, mounted on the second side of the attachment base and built into the standoff assembly, that receives and engages the pull-tab from the other component and into which the pull-tab from the other component has been placed,
wherein each pull-tab has a length sufficient to reach and be received by the female connective element of the other closure component, the second end of the pull-tab protruding from the female connective element;
wherein, when the assembled pair is affixed to the skin with each of the attachment bases disposed on an opposite side of the tissue opening, the second ends of the pull-tabs can be pulled away from each other, to bring the sloped portions of the forward faces of the components into substantial contact with one another at a location of contact and to cause each standoff assembly to pivot about the location of contact, so as to induce eversion of tissue edges that defined the opening; and
an applicator tool for applying the tissue closure devices to the tissue opening, the tool comprising:
an operator end configured to be grasped by a user;
a pair of arms configured to adjust spacing between the arms while maintaining the arms in parallel alignment;
wherein the arms are attached to corresponding second ends of pull-tabs of each of the closure device such that the devices straddle the arms of the applicator tool, and
wherein the applicator tool moves between a first position to a second position, the second position in which the pull-tabs on one side have been pulled away from those on the other side, after the devices have been placed on the tissue opening and the operator chooses to effectuate tissue closure.

11. A method of closing a tissue opening of a patient using the system of claim 10, the method comprising;
affixing the assembled pair of each device such that each of their attachment bases is disposed on an opposite side of the tissue opening;
loading the openings of the second ends of the closure device onto corresponding arms of the applicator tool, the applicator tool in a first position;
moving the applicator tool from the first position to the second position.

12. The method of claim 11, further comprising cutting the application tool from the closure devices.

* * * * *